United States Patent [19]

Sanders

[11] Patent Number: 5,635,447

[45] Date of Patent: Jun. 3, 1997

[54] POLYORGANIC ACIDS AND THEIR ANALOGUES TO ENHANCE HERBICIDE EFFECTIVENESS

[75] Inventor: J. Larry Sanders, Bedford Park, Ill.

[73] Assignee: Donlar Corporation, Bedford Park, Ill.

[21] Appl. No.: 621,840

[22] Filed: Mar. 22, 1996

[51] Int. Cl.[6] .......................... A01N 33/00; A01N 37/22; A01N 43/10; A01N 43/68; A01N 43/80; A01N 43/84; A01N 47/10; A01N 47/28

[52] U.S. Cl. .......................... 504/134; 504/118; 504/119; 504/127; 504/129; 504/133; 504/143; 504/189; 504/201; 504/206; 504/223; 504/224; 504/225; 504/226; 504/227; 504/229; 504/231; 504/232; 504/233; 504/234; 504/250; 504/271; 504/288; 504/289; 504/300; 504/320; 504/323; 504/324; 504/326; 504/327; 504/330; 504/334; 504/339; 504/340; 504/341; 504/342; 504/347; 71/DIG. 1

[58] Field of Search ..................... 504/118, 119, 504/127, 129, 133, 134, 143, 149, 189, 201, 206, 223–226, 227–229, 231–234, 250, 271, 288, 289, 300, 320, 323, 324, 326, 327, 330, 334, 339–342, 347; 71/DIG. 1

[56] References Cited

U.S. PATENT DOCUMENTS

| | | | |
|---|---|---|---|
| 5,350,735 | 9/1994 | Kinnersley et al. | 504/147 |
| 5,360,892 | 11/1994 | Bonsignore et al. | 528/354 |
| 5,457,176 | 10/1995 | Adler et al. | 528/328 |
| 5,580,840 | 12/1996 | Harms et al. | 504/115 |
| 5,593,947 | 1/1997 | Kinnersley et al. | 504/283 |

FOREIGN PATENT DOCUMENTS 5246863  9/1993  Japan.

OTHER PUBLICATIONS

CAPLUS Abstract Accession No. 1995:616583 (1995).
WPIDS Abstract Accession No. 93–339638 (1993).
Sinclair, Richard G., "Slow release Pesticide system . . . " Environmental Science & Technology, vol. 7(10), 1973, pp. 955–956.
Turner, D.J. et al., "Complexing agents as herbicide additives," Weed Research, vol. 18, 1978, pp. 199–207.
Technological Breakthrough on Fertilizer Use, AGRI FINANCE Apr. 1993 pp. 16–17.
Kinnersley et al., Plant Growth Regulation (9:137–146 (1990)).

*Primary Examiner*—John Pak
*Attorney, Agent, or Firm*—Zarley, McKee, Thomte, Voorhees, & Sease

[57] ABSTRACT

A herbicide composition which comprises a herbicide and a small but herbicide absorption enhancing effective amount of a water soluble, non-aromatic polyorganic acid or a salt or copolymer thereof such as polyaspartic acid.

22 Claims, No Drawings

POLYORGANIC ACIDS AND THEIR ANALOGUES TO ENHANCE HERBICIDE EFFECTIVENESS

BACKGROUND OF THE INVENTION

This invention relates to herbicides. More particularly, in a preferred aspect it relates to an improved method for enhancing effectiveness of herbicide absorption by weeds to effect a kill.

Herbicides with which this invention may be used are well known classes of herbicides. The precise herbicide itself forms no part of the invention. Suitable herbicides may be substituted urea herbicides, carbamate herbicides, chloro acetamides, triazines, acetanilides, morpholine derivatives, toluidines, clomazone derivatives and the like.

These classes of herbicides are known in the art and are sold under a variety of trademarks such as Harness®, Dual II®, Frontier®, Extrazine®, Command®, Canopy®, Sencor®, Lasso®, Prowl®, Eradicane®, Atrazine®, and Dual®, to name a few. In the broad chemical sense, most of these are classified as substituted urea herbicides, carbamate and thiocarbamate herbicides, chlorohydrocarbons, triazines, toluidines, clomazone derivatives, morpholines and/or acetanilides.

While the above have been shown to be effective herbicides, they also are known to have some environmental risks, such as a pollution risk. In order to minimize environmental risks such as pollution risks, effort always continues towards increasing the effectiveness of known herbicides from the standpoint of the ability to achieve the same level of effectiveness, but with less herbicide active component.

Accordingly, it is a primary objective of the present invention to provide a composition which enhances the effectiveness of certain classic types of herbicides, particularly the preferred urea herbicides such as Diuron®, carbamate and thio carbamate herbicides such as Sutan®, chloro acetamides such as Metolachlor®, acetanilides such as Alachlor®, and morpholine derivatives such as dimethomorph.

Yet another objective of the present invention is to achieve enhanced effectiveness of herbicides by enhancing the ability of the herbicide to be absorbed by the exterior cell membrane layers of weeds, thereby substantially increasing the effectiveness, and thus allowing reduction of the treatment level required in field application.

Still another objective of the present invention is to provide a herbicide effectiveness enhancing composition which uses as an additive a pollution- free additive that is environmentally unobjectionable.

And, a further objective is to improve penetration of the herbicide into the week tissue in adverse weather conditions such as drought or extended periods of low rainfall.

The method and means of accomplishing each of the above objectives will become apparent from the detailed description of the invention which follows.

SUMMARY OF THE INVENTION

A herbicide composition which comprises herbicides such as urea herbicides, carbamate herbicides, chloro acetamide herbicides, acetanalides, and morpholine derivatives, in combination with an absorption enhancing effective amount of a water soluble non-aromatic polyorganic acid or salt form of such an acid. Particularly preferred is polyaspartic acid. The invention in a broader aspect also involves a method of enhancing the dose effectiveness of certain classes of herbicides by adding to those a cell membrane penetration effectiveness aid, such as polyaspartic acid.

DETAILED DESCRIPTION OF THE INVENTION

The present invention is premised upon the fact that it has been discovered that certain compounds, namely certain polymeric organic amino acids, as set forth in earlier commonly-owned U.S. Pat. Pat. No. 5,350,735, which, along with each of its continuation-in-part applications, namely Ser. No. 08/313,436, filed Sep. 27, 1994, which is now U.S. Pat. No. 5,593,947, Ser. No. 08/439,279, filed May 11, 1995, which is now U.S. Pat. No. 5,580,840, and Ser. No. 08/447,784, filed May 23, 1995, all of which disclosures are incorporated herein by reference, can be used effectively in enhancing the penetration of herbicides such as urea herbicides through the exterior surface cells of a weed.

The invention, of course, is not limited to the treatment of any specific weed, but can be used effectively for treating any of the common weeds for any agricultural or horticultural crop, including fruits, cereals, vegetables, flowers and ornamentals. The invention is also useful for any application in post emergence situations where herbicides are used for control of weeds, such as in lawns and gardens, around homes and farm buildings, grain elevators, in greenhouses, etc. Examples of post emergence herbicides useful in the combinations of the invention include Banvel®, a salt of dicamba, paraquat dichloride, glyphosate, 2,4-dichlorophenoxyacetic acid and conventionally used herbicidal oils.

In general, the polymeric organic acid can be simply added to the liquid form of the herbicide, generally within a weight ratio of from 1:100 (polyaspartate:insecticide) to 100:1 (polyaspartate:insecticide).

The polymeric organic acids, suitable for the practice of the present invention, must be water soluble, non-aromatic, and must have a molecular weight sufficiently large to preclude absorption into the system of plants. To that end, the non-aromatic polymeric organic acid units (residues), or mers, in the linear polymer chain that constitutes the polymeric acid organic acids having a molecular weight in excess of about 100,000, usually exhibit poor solubility in water for the present purposes. Thus, for present purposes, a polymeric organic acid molecular weight not larger than about 100,000 is preferred. Particularly, preferred molecular weight is in the range of about 1,500 to about 100,000.

Illustrative are polymeric organic acids, with or without carboxylic acid, thiocarboxylic acid, imidocarboxy, and/or amino side chains such as, for example, polyacrylic acid, polyiticonic acid, polyepoxysuccinic acid, polymethylacrylic acid, polymaleic acid, polyfumaric acid, polylysine, polyglutamic acid, polyaspartic acid, polyglycine, polycysteine, polycysteine/glutamic acid, mixtures of the foregoing or their salts, copolymers of the above, and the like. Thus, block or random copolymers or terpolymers of several organic acids are also within the purview of the present invention as the polymeric acid component thereof. For example, the utilized polymeric acid component can be a block copolymer of aspartic acid residues and L-lactic acid residues, a random copolymer of aspartic acid residues and glycolic acid residues, a conjugated protein constituted by amino acid residue chains interconnected by one or more polycarboxylic acid residues, a copolymer of acrylic acid and acrylamide, and the like.

Polymers of organic acids are commercially available. In addition, such polymeric acids, especially poly(amino acids), can be made inter alia, by thermal condensation methods. See, for example, U.S. Pat. No. 5,057,597 to Koskan, Little et al., American Chemical Society 97: 263–279 (1991), and U.S. Pat. No. 4,696,981 to Harada et al.

While the above description has been presented with particular mention of classic herbicides such as Atrazine®, Lasso® and Dual II®, other well known herbicides can be used with the same observed enhanced effectiveness, as shown in the specific working examples below.

The herbicide, in combination with the polyorganic acid or salt, such as polyaspartic acid, may be applied by direct spray, dusting, drenching, may be applied in granular form, as a wet powder, an aerosol, by soil application or leaf application. It may be used as a preemergent or postemergent application, depending on the herbicide chosen. In short, the application method is not critical.

The crop plants for which the herbicides may be used are not critical, and generally include any of the commonly used domesticated grain, row crops, and as well, fruit and vegetables. Such crops may be corn, soybeans, alfalfa, wheat, oats, potatoes, apples, oranges, tomatoes, green beans, and in general include monocotyledons and dicotyledons.

The following examples are offered to further illustrate, but not necessarily limit the process and to demonstrate the compositions of the present invention as showing enhanced herbicide effectiveness in comparison with herbicide alone. It will be apparent to those of ordinary skill in the art that certain modifications can be made to the process and composition without departing from the spirit and scope of the invention here described.

EXAMPLES 1–7, Table I

In the following examples, classic herbicides were demonstrated as more effective in combination with the polyorganic acids, and particularly polyaspartic acid of the present invention, in potted plant experiments. In these experiments, 25 ppm of polyaspartic acid, molecular weight 5,000, were mixed on a weight-by-weight basis with the potting soil. Wheat was planted into the pot, and herbicide applied to the pot as a spray at the level 0.05 pounds per acre to 0.1 pounds per acre, and each pot was watered to activate the herbicide within the pot. Weed counts were taken over time at two week intervals to determine the amount of biomass reduction.

As demonstrated in Table I below, the herbicides were shown to be effective against broadleaf weeds, grasses, annual grasses, in both preemergence and early emergence environments.

TABLE I

| Herbicide | Weed | Application Level Lb ai/A | Biomass Reduction Alone | Biomass Reduction With PA |
| --- | --- | --- | --- | --- |
| Harness ® | Giant Foxtail | .03 | 45 | 90 |
| Dual II ® | Giant Foxtail | .07 | 61 | 89 |
| Frontier ® | Giant Foxtail | .04 | 78 | 92 |
| Extrazine ® | Giant Foxtail | .25 | 62 | 97 |
| Harness ® | Velvet Leaf | 1.0 | 70 | 90 |
| Atrazine ® | Velvet | .25 | 46 | 95 |

TABLE I-continued

| Herbicide | Weed | Application Level Lb ai/A | Biomass Reduction Alone | Biomass Reduction With PA |
| --- | --- | --- | --- | --- |
| Extrazine ® | Leaf Velvet Leaf | .3 | 29 | 99 |

EXAMPLES 8–11, Table II

For effectiveness, actual field data was checked to confirm the greenhouse pot experiments of examples 1–7. In particular, polyaspartic acid, molecular weight 5,000, was applied at a level of 2 quarts per acre to soybeans and lightly disked into the soil. The herbicide was applied at the conventional labeled recommended rate. The results are reported in Table II.

TABLE II

| | Field Data Soybeans | |
| --- | --- | --- |
| Herbicide | Yield Alone (Per Acre) | Yield Plus Polyaspartic Acid |
| Command ®/Canopy ® | 47 bu/acre | 58 bu/acre |
| Command ®/Sencor ® | 51 bu/acre | 56 bu/acre |
| Lasso ® | 58 bu/acre | 63 bu/acre |
| Prowl ® | 38 bu/acre | 51 bu/acre |

A similar procedure, to Table II experiments 8–11 was conducted in the State of Illinois with corn. Table III reports the results. Again, the recommended dosage rate of the particular herbicides was followed in terms of rate of application per acre, and the amount of polyaspartic acid used was as reported in the Table II experiments.

EXAMPLES 12–16, Table III

TABLE III

| | FIELD DATA CORN | |
| --- | --- | --- |
| Herbicide | Yield w/o Polyaspartic Acid | Yield With Polyaspartic Acid |
| Eradicane ®/Atrazine ® | 178 bu/acre | 184 bu/acre |
| Extrazine ® | 188 bu/acre | 199 bu/acre |
| Dual ®/Atrazine ® | 168 bu/acre | 180 bu/acre |
| Frontier ®/Atrazine ® | 136 bu/acre | 146 bu/acre |

As seen from the above examples, the polyaspartic acid significantly enhances the absorption, and therefore the effectiveness of the herbicide. Generally, the polyaspartic acid should be dosed in combination with the herbicide at a rate of from about 0.01 gallons per acre to 5.0 gallons per acre, with the most desirable being approximately 0.5 gallons per acre. The amount of solids of the polyacid in solution should generally be within the range of from 20% solids to 60% solids, generally from 40% solids to 42% solids. The preferred polyaspartic acid is that having an average molecular weight of 5,000.

What is claimed is:

1. A herbicide composition which comprises:
a herbicide, and a small but herbicide absorption enhancing effective amount of water soluble polyaspartic acid, and its salts or copolymers.

2. A herbicide solution composition which comprises:

a herbicide solution, and a small but herbicide absorption enhancing effective amount of a water soluble, non-aromatic, polyorganic acid or salt thereof which is a polyamino acid or a copolymer of said acid, or salt thereof with the acid being polyaspartic acid, said polyaspartic acid having a molecular weight larger than 1500.

3. The herbicide composition of claim 1 wherein the herbicide is selected from the group consisting of substituted urea herbicides, carbamate herbicides, chloroacetamides, triazines, acetanilides, morpholine derivatives, toluidines and clomazone derivatives.

4. The herbicide composition of claim 2 wherein the herbicide is a substituted urea based herbicide.

5. The composition of claim 2 wherein the herbicide is a carbamate.

6. The composition of claim 2 wherein the herbicide is a chloroacetamide.

7. The herbicide composition of claim 2 wherein the polyaspartic acid has a molecular weight in the range of about 1500 to about 100,000.

8. The herbicide composition of claim 7 wherein the polyaspartic acid has a molecular weight in the range of about 3000 to 40,000.

9. The herbicide composition of claim 1 wherein the amount of polyaspartic acid or salt form thereof is from a weight ratio of about 1:100 (polyaspartic acid or salt : herbicide) to about 100:1 (polyaspartic acid or salt : herbicide).

10. The herbicide composition of claim 1 wherein the amount of polyaspartic acid or salt form thereof is from about 1:100 (polyaspartic acid or salt : herbicide) to about 20:1 (polyaspartic acid or salt : herbicide).

11. The herbicide composition of claim 2 wherein the herbicide is a urea herbicide and the polyorganic acid or salt form thereof is polyaspartic acid having a molecular weight of from 3000 to 40,000.

12. The herbicide composition of claim 2 wherein the herbicide is a carbamate and the polyorganic acid or salt form thereof is polyaspartic acid having a molecular weight of from 3000 to 40,000.

13. The herbicide composition of claim 2 wherein the herbicide is a chloroacetamide and the polyorganic acid or salt form thereof is polyaspartic acid having a molecular weight of from 3000 to 40,000.

14. A method of enhancing the absorption effectiveness of herbicides, said method comprising:

adding to a herbicide a small but herbicide absorption enhancing effective amount of a water soluble, non-aromatic polyorganic acid or salt form thereof which is a polyamino acid or a copolymer of said acid, or salt thereof, selected from the group consisting of polyaspartic acid, polyglutamic acid, polyglycine, polylysine, a copolymer of cysteine and glutamic acid and a terpolymer of cysteine, glutamic acid and aspartic acid, and salt form thereof said polyamino acid having a molecular weight larger than 1500.

15. The method of claim 14 wherein the polyamino acid is polyaspartic acid.

16. The method of claim 14 wherein the polyaspartic acid has a molecular weight in the range of about 1500 to 100,000.

17. The method of claim 14 wherein the polyamino acid is polyaspartic acid having a molecular weight in the range of about 3000 to 40,000.

18. The method of claim 14 wherein the amount of polyaspartic acid or salt form thereof is from a weight ratio of about 1:100 (polyaspartic acid or salt : herbicide) to about 100:1 (polyaspartic acid or salt : herbicide).

19. The method of claim 14 wherein the amount of polyaspartic acid or salt form thereof is from about 1:100 (polyaspartic acid or salt : herbicide) to about 20:1 (polyaspartic acid or salt : herbicide).

20. The method of claim 14 wherein the herbicide is a urea based herbicide and the polyorganic acid or salt form thereof is polyaspartic acid having a molecular weight of from 3000 to 40,000.

21. The method of claim 14 wherein the herbicide is a carbamate and the polyorganic acid or salt form thereof is polyaspartic acid having a molecular weight of from 3000 to 40,000.

22. The method of claim 14 wherein the herbicide is an acetanilide and the polyorganic acid or salt form thereof is polyaspartic acid having a molecular weight of from 3000 to 40,000.

* * * * *